US008664414B2

(12) United States Patent
Nagato et al.

(10) Patent No.: US 8,664,414 B2

(45) Date of Patent: Mar. 4, 2014

(54) PROCESS FOR PRODUCING EPOXY COMPOUND

(75) Inventors: Nobuyuki Nagato, Minato-ku (JP); Hiroshi Uchida, Minato-ku (JP); Katsura Horikoshi, Minato-ku (JP); Mitsuhiro Imaizumi, Minato-ku (JP)

(73) Assignee: Showa Denko K.K., Tokyo (JP)

( * ) Notice: Subject to any disclaimer, the term of this patent is extended or adjusted under 35 U.S.C. 154(b) by 203 days.

(21) Appl. No.: 13/256,863

(22) PCT Filed: Mar. 17, 2010

(86) PCT No.: PCT/JP2010/054592

§ 371 (c)(1), (2), (4) Date: Sep. 15, 2011

(87) PCT Pub. No.: WO2010/110151

PCT Pub. Date: Sep. 30, 2010

(65) Prior Publication Data

US 2012/0029217 A1 Feb. 2, 2012

(30) Foreign Application Priority Data

Mar. 25, 2009 (JP) ................................ 2009-074642

(51) Int. Cl.
*C07D 301/12* (2006.01)

(52) U.S. Cl.
USPC ........................................................ 549/531

(58) Field of Classification Search
USPC ........................................................ 549/531
See application file for complete search history.

(56) References Cited

U.S. PATENT DOCUMENTS

| | | | |
|---|---|---|---|
| 4,937,216 A | 6/1990 | Clerici et al. | |
| 6,037,484 A | 3/2000 | Grey | |
| 7,074,947 B2 * | 7/2006 | Hirota et al. | 549/531 |
| 2005/0020841 A1 | 1/2005 | Hirota et al. | |
| 2007/0117993 A1 | 5/2007 | Hori et al. | |
| 2009/0030217 A1 | 1/2009 | Uchida et al. | |

FOREIGN PATENT DOCUMENTS

| | | | |
|---|---|---|---|
| EP | 0 230 949 | A2 | 8/1987 |
| JP | 59-227872 | A | 12/1984 |
| JP | 62-114979 | A | 5/1987 |
| JP | 62-185081 | A | 6/1987 |
| JP | 05-059033 | A | 3/1993 |
| JP | 07-145157 | * | 6/1995 |
| JP | 07-145157 | A | 6/1995 |
| JP | 08/027136 | A | 1/1996 |
| JP | 2001-025665 | A | 1/2001 |
| JP | 2002-526483 | A | 8/2002 |
| JP | 2003-192679 | A | 7/2003 |
| JP | 2003-300971 | A | 10/2003 |
| JP | 2004-059573 | A | 2/2004 |
| JP | 2004-115455 | A | 4/2004 |
| JP | 2005-169363 | A | 6/2005 |
| JP | 2006-316034 | A | 11/2006 |
| JP | 2008-120766 | A | 5/2008 |
| JP | 2008-239579 | A | 10/2008 |

OTHER PUBLICATIONS

Chemical Abstracts, Inorganic Anal. Chem., 1984, p. 579, vol. 101, 23239c.

Payne, George B., et al., "Reactions of Hydrogen Peroxide, VII, Alkali-Catalyzed Epoxidation and Oxidation Using a Nitrile as Co-reactant", The Journal of Organic Chemistry, Mar. 1961, pp. 659-663, vol. 26, No. 3.

Ishii, Yasutaka, et al., "Hydrogen Peroxide Oxidation Catalyzed by Heteropoly Acids Combined with Cetylpyridinium Chloride: Epoxidation of Olefins nd Allylic Alcohols, Ketoniation of Alochols and Diols, and Oxidative Cleavage of 1,2-Diols and Olefins", Journal of Organic Chemistry, 1988, pp. 3587-3593, vol. 53, No. 15.

Van Vilet, Michiel C. A., et al, "Perfluoroheptadecan-9-one: a selective and reusable catalyst for epoxidations with hydrogen peroxide", Chem. Commun., 1999, pp. 263-264.

Bach, R.D., et al., "Epoxidation of Olefins by Hydrogen Peroxide-Acetonitrile: cis-Cyclooctene Oxide", Organic Syntheses, 1981, pp. 63-66, vol. 60.

* cited by examiner

*Primary Examiner* — Taylor Victor Oh

(74) *Attorney, Agent, or Firm* — Sughrue Mion, PLLC

(57) ABSTRACT

According to the present invention, a process for producing an epoxy compound, where an epoxy compound can be selectively produced from olefins with good yield at low cost in a safe manner by a simple operation under mild conditions without using a quaternary ammonium salt or a metal compound, is provided. The present invention relates to a process for producing an epoxy compound, comprising epoxidizing a carbon-carbon double bond of an organic compound having a carbon-carbon double bond by using hydrogen peroxide as an oxidant, wherein the epoxidation is carried by out using an organic nitrile compound and an organic amine compound.

38 Claims, No Drawings

PROCESS FOR PRODUCING EPOXY COMPOUND

CROSS REFERENCE TO RELATED APPLICATION

This application is a National Stage of International Application No. PCT/JP2010/054592 filed Mar. 17, 2010, the contents of which are incorporated herein by reference in their entirety.

TECHNICAL FIELD

The present invention relates to a process for producing an epoxy compound. More specifically, the present invention relates to a process for producing an epoxy compound, where a carbon-carbon double bond of an organic compound (olefin) having a carbon-carbon double bond can be epoxidized with high efficiency by using hydrogen peroxide as an oxidant in the presence of an organic nitrile compound and an organic amine compound.

BACKGROUND ART

Hydrogen peroxide is inexpensive, non-corrosive and environmentally-friendly because only water is produced as a by-product after reaction, and is an excellent oxidant for use in industry.

As a process for producing an epoxy compound from olefins by using hydrogen peroxide as an epoxidizing agent (oxidant), there have been conventionally known: (1) an epoxidation process by using hydrogen peroxide in the presence of quaternary ammonium chloride, phosphoric acids and a tungsten metal salt (see, Patent Documents 1 and 2 below); (2) an epoxidation process in an organic solvent by using a phase transfer catalyst, such as a quaternary ammonium salt, and using, as catalysts, tungstic acids and α-aminomethylphosphonic acid (see, Patent Document 3 below); (3) an epoxidation process in a toluene solvent in the presence of quaternary ammonium hydrogensulfate, phosphoric acids and a tungsten oxide compound obtained by reacting a tungsten compound with hydrogen peroxide (see, Patent Document 4 below); (4) an epoxidation process by using a multicomponent oxidation catalyst containing a tungsten compound, a quaternary ammonium salt, phosphoric acids and/or boric acids, and hydrogen sulfate in the presence of an organic solvent, such as toluene (see, Patent Document 5 below); and (5) an epoxidation process in a chloroform solvent by using a catalyst having both phase transfer ability and epoxidation ability, such as a cetylpyridinium salt of a heteropoly acid (see, Non-Patent Document 1 below). However, these catalyst systems involve use of an organic solvent, and moreover, use of a quaternary ammonium salt, and therefore suffer from the problem that a quaternary ammonium salt-derived impurity is unavoidably mixed in an organic reaction solution to deteriorate the quality. In addition, due to a quaternary ammonium salt-derived decomposition product, an epoxy group causes cationic polymerization during distillation for purification. A reaction system where a reaction proceeds without using an organic solvent has been also reported (see, Patent Document 6 below). However, this system substantially has the same problem, though an organic solvent needs not be used in the reaction.

As a process using a catalyst other than a tungsten compound, there are known: (6) an epoxidation process by using hydrogen peroxide and using a catalyst prepared by loading methyl trioxorhenium ($CH_3ReO_3$) and a strong organic base compound on an inorganic oxide support (see, Patent Document 7 below); (7) an epoxidation process by using hydrogen peroxide in the presence of a titanium-containing zeolite catalyst and an additive containing a tertiary amine, a tertiary amine oxide or a mixture thereof (see, Patent Document 8 below); and (8) an epoxidation process by using hydrogen peroxide in the presence of a fluoroalkyl ketone (see, Non-Patent Document 2 below). However, these processes are a process having low catalytic efficiency, requiring an excess of hydrogen peroxide, and being subject to many restrictions, such as applicability only to a small molecule substrate.

A process of reacting hydrogen peroxide and an organic nitrile compound with a carbon-carbon double bond in the presence of a carbonate, hydrogencarbonate or the like of an alkali metal is also known (see, Non-Patent Document 3 and Patent Document 9, below). However, this process has a problem that not only contamination of a slight amount of an alkali metal is unavoidable but also particularly when a compound having an ester bond is employed, the ester bond is liable to be hydrolyzed with the alkali metal salt during epoxidation reaction and purification, leading to reduction in the yield.

RELATED ART

Patent Document

Patent Document 1: Kokai (Japanese Unexamined Patent Publication) No. 2004-115455

Patent Document 2: Kokai No. 2003-192679

Patent Document 3: Kokai No. H8-27136

Patent Document 4: Kokai No. 2004-59573

Patent Document 5: Kokai No. 2005-169363

Patent Document 6: Kokai No. 2006-316034

Patent Document 7: Kokai No. 2001-25665

Patent Document 8: Kohyo (National Publication of Translated Version) No. 2002-526483

Patent Document 9: Kokai No. 2008-239579

Non-Patent Document

Non-Patent Document 1: J. Org. Chem., Vol. 53, No. 15, 3587-3593 (1988)

Non-Patent Document 2: Chem. Commun., 263-264 (1999)

Non-Patent Document 3: Organic Synthesis, Vol. 60, 63-66 (1981)

Accordingly, developing a process for selectively producing an epoxy compound from olefins with good yield at a low cost in a safe manner by a simple operation under mild conditions without using a compound that may contaminate the product has been strongly demanded.

SUMMARY OF THE INVENTION

Problems to be Solved by the Invention

An object of the present invention is to provide a process for producing an epoxy compound, where an epoxy compound can be selectively produced from olefins with good yield at a low cost in a safe manner by a simple operation under mild conditions without using a quaternary ammonium salt or a metal compound.

Means for Solving the Problems

As a result of intensive studies to attain the above-described object, the present inventors have found that according to the following process, an epoxy compound is selectively produced with high efficiency from a compound having a carbon-carbon double bond by using hydrogen peroxide. The present invention has been accomplished based on this finding.

Specifically, the present invention includes the following [1] to [12].

[1] A process for producing an epoxy compound, comprising epoxidizing a carbon-carbon double bond of an organic compound having a carbon-carbon double bond by using hydrogen peroxide as an oxidant, wherein the epoxidation is carried out by using an organic nitrile compound and an organic amine compound.

[2] The process for producing an epoxy compound as described in [1] above, wherein the organic nitrile compound is at least one member selected from acetonitrile, propionitrile, butyronitrile, isobutyronitrile, benzonitrile and trichloroacetonitrile.

[3] The process for producing an epoxy compound as described in [1] or [2] above, wherein the organic amine compound contains a tertiary amine.

[4] The process for producing an epoxy compound as described in any one of [1] to [3] above, wherein the organic compound having a carbon-carbon double bond is an organic compound having a cyclohexene skeleton.

[5] The process for producing an epoxy compound as described in any one of [1] to [4] above, wherein the organic compound having a carbon-carbon double bond is at least one compound represented by the following formula (1):

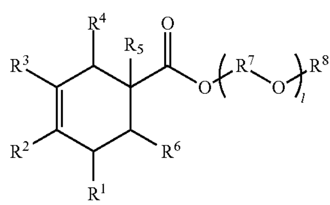

{wherein each of $R^1$, $R^2$, $R^3$, $R^4$ and $R^5$ is independently a hydrogen atom or a methyl group, $R^6$ is a hydrogen atom, a methyl group, a phenyl group or $R^9$ represented by the following formula (2):

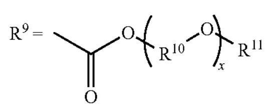

(wherein $R^{10}$ is an alkylene group having a carbon number of 2 to 8 or a cycloalkylene group having a carbon number of 4 to 8, $R^{11}$ is an alkyl group having a carbon number of 1 to 10, a cycloalkyl group having a carbon number of 4 to 8, an aryl group having a carbon number of 6 to 10, an alkenyl group having a carbon number of 2 to 10 or a cycloalkenyl group having a carbon number of 4 to 8, and x is an integer of 0 to 5), $R^7$ is an alkylene group having a carbon number of 2 to 8 or a cycloalkylene group having a carbon number of 4 to 8, $R^8$ is an alkyl group having a carbon number of 1 to 10, a cycloalkyl group having a carbon number of 4 to 8, an aryl group having a carbon number of 6 to 10, an alkenyl group having a carbon number of 2 to 10 or a cycloalkenyl group having a carbon number of 4 to 8, and l is an integer of 0 to 5} and/or the following formula (3):

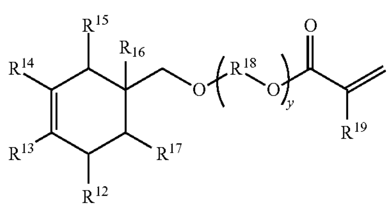

{wherein each of $R^{12}$, $R^{13}$, $R^{14}$, $R^{15}$, $R^{16}$ and $R^{17}$ is independently a hydrogen atom or a methyl group, $R^{18}$ is an alkylene group having a carbon number of 2 to 8 or a cycloalkylene group having a carbon number of 4 to 8, $R^{19}$ is a hydrogen atom, a methyl group or a phenyl group, and y is an integer of 0 to 5}.

[6] The process for producing an epoxy compound as descried in any one of [1] to [3] above, wherein the organic compound having a carbon-carbon double bond is an organic compound having an allyl ether bond.

[7] The process for producing an epoxy compound as described in any one of [1] to [3] and [6] above, wherein the organic compound having a carbon-carbon double bond has a structure represented by the following formula (4):

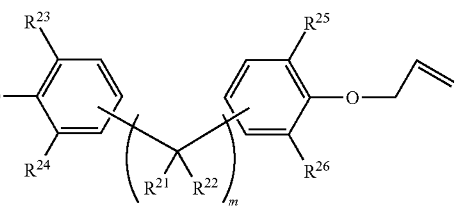

{wherein each of $R^{21}$ and $R^{22}$ is independently a hydrogen atom, an alkyl group having a carbon number of 1 to 6, a cycloalkyl group having a carbon number of 3 to 12 or an aryl group having a carbon number of 6 to 10, or $R^{21}$ and $R^{22}$ may combine together to form a cycloalkyl group having a carbon number of 3 to 12, each of $R^{23}$, $R^{24}$, $R^{25}$ and $R^{26}$ is independently a hydrogen atom, an alkyl group having a carbon number of 1 to 10, a cycloalkyl group having a carbon number of 3 to 12 or an aryl group having a carbon number of 6 to 10, and m represents an integer of 0 or 1}.

[8] The process for producing an epoxy compound as described in [6] above, wherein the compound having an allyl ether bond is at least one member selected from the group consisting of a diallyl ether of bisphenol-A, a diallyl ether of bisphenol-F, and 3,3'-5,5'-tetramethyl-4,4'-biphenyldiol diallyl ether.

[9] The process for producing an epoxy compound as described in [6] above, wherein the compound having an allyl ether bond is at least one member selected from the group consisting of an $\alpha,\omega$-polyalkyleneglycol diallyl ether having a carbon number of 2 to 20, 1,4-cyclohexanedimethanol diallyl ether and tricyclo[$5.2.1.0^{2,6}$]decanedimethanol diallyl ether.

[10] The process for producing an epoxy compound as described in any one of [1] to [9] above, wherein the organic nitrile compound is used for the organic compound having a carbon-carbon double bond to be epoxidized so that a nitrile group in the organic nitrile compound is in a ratio of 0.8 to 40 molar equivalents based on the number of carbon-carbon double bonds of the organic compound.

[11] The process for producing an epoxy compound as described in any one of [1] to [10] above, wherein the hydrogen peroxide is an aqueous hydrogen peroxide solution at 20 to 65 mass %.

[12] The process for producing an epoxy compound as described in any one of [1] to [11] above, wherein the organic amine compound is used for the organic compound having a carbon-carbon double bond to be epoxidized so that an amine group in the organic amine compound is in a ratio of 0.001 to 2 molar equivalents based on the number of carbon-carbon double bonds of the organic compound.

Effect of the Invention

According to the process for producing an epoxy compound of the present invention, a tungsten compound, a quaternary ammonium salt, an alkali metal salt and other metal-containing catalytic components need not be used, and therefore, the catalytic component from the organic substrate after reaction can be easily separated. In addition, according to the process for producing an epoxy compound of the present invention, a polyfunctional epoxy monomer that is widely used in various industrial fields including chemical industry as a raw material of resist materials (particularly, solder resist materials) or as a raw material of various polymers, such as agricultural/pharmaceutical intermediate, plasticizer, adhesive and coating resin, can be safely produced through a reaction of corresponding polyolefins with hydrogen peroxide by a simple operation with good yield at a low cost. For these reasons, the present invention brings numerous benefits to the industry. Furthermore, the process for producing an epoxy compound of the present invention does not use an organic solvent and therefore, also has an effect of reducing the burden on the environment.

MODE FOR CARRYING OUT THE INVENTION

The present invention is described in detail below.

In the process for producing an epoxy compound of the present invention, hydrogen peroxide is used as an oxidant, and an aqueous hydrogen peroxide solution is suitably used. The concentration of the aqueous hydrogen peroxide solution is not particularly limited but is generally selected from the range of 1 to 80 mass % and preferably the range of 20 to 65 mass %. The concentration of hydrogen peroxide is of course preferably high in view of industrial productivity and energy cost at the separation, but needless to say, it is preferable not to use excessive hydrogen peroxide at an unnecessarily high concentration.

The amount of the aqueous hydrogen peroxide solution used is also not particularly limited, but if the aqueous solution is used in excess, the production amount of an amide compound as a by-product is increased due to the reaction of excessive hydrogen peroxide and the organic nitrile compound. Furthermore, when hydrogen peroxide used in excess remains, this brings about a problem in the treatment of hydrogen peroxide after reaction. For these reasons, the amount of the aqueous hydrogen peroxide solution used for the organic compound (olefin) to be epoxidized is preferably from 0.5 to 10 molar equivalents, more preferably from 0.7 to 5 molar equivalents, based on the number of carbon-carbon double bonds of the organic compound.

Examples of the organic nitrile compound used in the process for producing an epoxy compound of the present invention include acetonitrile, propionitrile, butyronitrile, isobutyronitrile, benzonitrile and trichloroacetonitrile, and at least one member selected therefrom may be used. It is considered that the organic nitrile compound reacts with hydrogen peroxide to form a reaction intermediate which acts as an oxidant, and on the other hand, the portion not participated in the reaction contributes as a solvent. In view of reaction results, benzonitrile and trichloroacetonitrile are preferred, but these nitrile compounds have a high boiling point and are difficult to separate from the product. In view of separation from the product, acetonitrile, propionitrile and isobutyronitrile are preferred, and among these, acetonitrile is more preferred, because this compound has a low boiling point and exhibits relatively high reactivity, though the reactivity is somewhat lower compared with benzonitrile and trichloroacetonitrile.

The amount of the nitrile group of the organic nitrile compound used is from 0.8 to 40 molar equivalents, preferably from 1.5 to 20 molar equivalents, based on the number of carbon-carbon double bonds of the organic compound (olefin) having a carbon-carbon double bond. If the amount of the nitrile group is less than 0.8 molar equivalents, the conversion ratio of the substrate is reduced, whereas if it exceeds 40 molar equivalents, the reaction disadvantageously proceeds at a low rate.

Examples of the organic amine compound used as a catalyst include methylamine, ethylamine, n-propylamine, isopropylamine, n-butylamine, isobutylamine, sec-butylamine, aniline, dimethylamine, diethylamine, di-n-propylamine, diisopropylamine, di-n-butylamine, diisobutylamine, di-sec-butylamine, trimethylamine, N,N-dimethylethylamine, N,N-diethylmethylamine, N-butyldimethylamine, N,N-dimethylisopropylamine, triethylamine, tri-n-propylamine, tri-n-butylamine, triisobutylamine, tri-n-pentylamine, triisoamylamine, tri-n-octylamine, tri-(2-ethylhexyl)amine, pyridine, 2-picolin, 3-picolin, 4-picolin, 1,8-diazabicyclo [5.4.0]undecene-7, and 1,5-diazabicyclo(4.3.0)nonene-5. Among these, in view of reactivity with the epoxy compound produced, catalytic activity and easy separation in the purification step, a tertiary amine having a boiling point of 50 to 200° C. is preferred, and examples thereof include N,N-diethylmethylamine, N-butyldimethylamine, N,N-dimethylisopropylamine, triethylamine, tri-n-propylamine and tri-n-butylamine.

The amount of the amine group in the organic amine compound used is from 0.001 to 2 molar equivalents, preferably from 0.05 to 0.3 molar equivalents, based on the number of carbon-carbon double bonds of the organic compound (olefin) having a carbon-carbon double bond. If the amount of the amine group is too small, the reaction rate is decreased, whereas if it is excessively large, the reaction of hydrogen peroxide only with a nitrile compound prevails and even when an epoxy compound is produced, the rate of a further side reaction is disadvantageously increased.

In the process for producing an epoxy compound of the present invention, the reaction is usually carried out in a temperature range of 0 to 150° C., preferably 20 to 100° C. The reaction time depends on the kind of the compound (olefin) having a carbon-carbon double bond used and the reaction temperature. For example, at temperature near 20° C., the conversion ratio is increased by carrying out the reaction over a few days, whereas at a temperature exceeding 100° C., unless the reaction is stopped in 1 to 2 hours, hydrolysis conspicuously occurs. The reaction time is generally from 2 to 100 hours, preferably from 5 to 40 hours.

Out of the compounds having a carbon-carbon double bond, in view of reactivity, a compound having a cyclohexene skeleton is preferred as the substrate to be epoxidized. Among these, the reaction is preferably carried out by using at least one compound represented by the following formula (1):

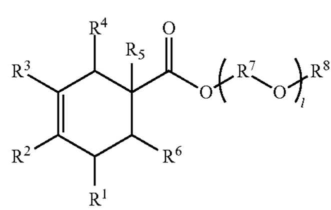

(1)

{wherein each of $R^1$, $R^2$, $R^3$, $R^4$ and $R^5$ is independently a hydrogen atom or a methyl group, $R^6$ is a hydrogen atom, a methyl group, a phenyl group or $R^9$ represented by the following formula (2):

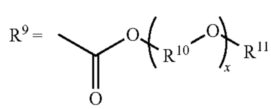

(2)

(wherein $R^{10}$ is an alkylene group having a carbon number of 2 to 8 or a cycloalkylene group having a carbon number of 4 to 8, $R^{11}$ is an alkyl group having a carbon number of 1 to 10, a cycloalkyl group having a carbon number of 4 to 8, an aryl group having a carbon number of 6 to 10, an alkenyl group having a carbon number of 2 to 10 or a cycloalkenyl group having a carbon number of 4 to 8, and x is an integer of 0 to 5), $R^7$ is an alkylene group having a carbon number of 2 to 8 or a cycloalkylene group having a carbon number of 4 to 8, $R^8$ is an alkyl group having a carbon number of 1 to 10, a cycloalkyl group having a carbon number of 4 to 8, an aryl group having a carbon number of 6 to 10, an alkenyl group having a carbon number of 2 to 10 or a cycloalkenyl group having a carbon number of 4 to 8, and l is an integer of 0 to 5} and/or the following formula (3):

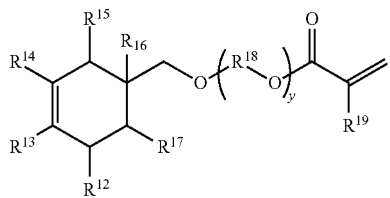

(3)

{wherein each of $R^{12}$, $R^{13}$, $R^{14}$, $R^{15}$, $R^{16}$ and $R^{17}$ is independently a hydrogen atom or a methyl group, $R^{18}$ is an alkylene group having a carbon number of 2 to 8 or a cycloalkylene group having a carbon number of 4 to 8, $R^{19}$ is a hydrogen atom, a methyl group or a phenyl group, and y is an integer of 0 to 5}.

Specific examples of the compound represented by formula (1) include methyl 3-cyclohexene-1-carboxylate, ethyl 3-cyclohexene-1-carboxylate, phenyl 3-cyclohexene-1-carboxylate, benzyl 3-cyclohexene-1-carboxylate, cyclohexyl 3-cyclohexene-1-carboxylate, allyl 3-cyclohexene-1-carboxylate, 2'-allyloxyethyl 3-cyclohexene-1-carboxylate, 2'-methyl-2'-propenyl 3-cyclohexene-1-carboxylate, 1'-methyl-2'-propenyl 3-cyclohexene-1-carboxylate, 1'-ethyl-2'-propenyl 3-cyclohexene-1-carboxylate, 1'-phenyl-2'-propenyl 3-cyclohexene-1-carboxylate, methyl 1-methyl-3-cyclohexene-1-carboxylate, ethyl 1-methyl-3-cyclohexene-1-carboxylate, phenyl 1-methyl-3-cyclohexene-1-carboxylate, benzyl 1-methyl-3-cyclohexene-1-carboxylate, cyclohexyl 1-methyl-3-cyclohexene-1-carboxylate, allyl 1-methyl-3-cyclohexene-1-carboxylate, 2'-allyloxyethyl 1-methyl-3-cyclohexene-1-carboxylate, methyl 3-cyclohexene-6-phenyl-1-carboxylate, ethyl 3-cyclohexene-6-phenyl-1-carboxylate, phenyl 3-cyclohexene-6-phenyl-1-carboxylate, benzyl 3-cyclohexene-6-phenyl-1-carboxylate, allyl 3-cyclohexene-6-phenyl-1-carboxylate, methyl 3-cyclohexene-3-methyl-1-carboxylate, ethyl 3-cyclohexene-3-methyl-1-carboxylate, phenyl 3-cyclohexene-3-methyl-1-carboxylate, benzyl 3-cyclohexene-3-methyl-1-carboxylate, allyl 3-cyclohexene-3-methyl-1-carboxylate, methyl 3-cyclohexene-4-methyl-1-carboxylate, ethyl 3-cyclohexene-4-methyl-1-carboxylate, phenyl 3-cyclohexene-4-methyl-1-carboxylate, benzyl 3-cyclohexene-4-methyl-1-carboxylate, allyl 3-cyclohexene-4-methyl-1-carboxylate, dimethyl 3-cyclohexene-1,6-dicarboxylate, diethyl 3-cyclohexene-1,6-dicarboxylate, diphenyl 3-cyclohexene-1,6-dicarboxylate, dibenzyl 3-cyclohexene-1,6-dicarboxylate, diallyl 3-cyclohexene-1,6-dicarboxylate, and 3-cyclohexenylmethyl 3-cyclohexene-1-carboxylate.

Examples of the compound represented by formula (3) include 3-cyclohexenylmethyl(meth)acrylate and 2-(3-cyclohexenylmethoxy)ethyl(meth)acrylate.

Among these, 3-cyclohexenylmethyl(meth)acrylate, allyl 3-cyclohexene-1-carboxylate and/or 3-cyclohexenylmethyl 3-cyclohexene-1-carboxylate are particularly preferred. Incidentally, examples of the compound having a cyclohexene skeleton other than the compound represented by formula (1) or (3) include vinylcyclohexene and limonene.

A compound having an allyl ether bond may be also used as the substrate to be epoxidized. The number of allyl ether bonds contained in the compound may be 1 or may be 2 or more. Examples of the compound where the number of allyl ether bonds is 1 include phenyl allyl ether, o-, m- or p-cresol monoallyl ether, biphenyl-2-ol monoallyl ether, biphenyl-4-ol monoallyl ether, butyl allyl ether, cyclohexyl allyl ether, and cyclohexanemethanol monoallyl ether.

Examples of the compound where the number of allyl ether bonds is 2 include α,ω-alkylenediol diallyl ethers having a carbon number of 2 to 20, such as 1,5-pentanediol diallyl ether, 1,6-hexanediol diallyl ether, 1,9-nonanediol diallyl ether, 1,10-decanediol diallyl ether and neopentylglycol diallyl ether, an α,ω-polyalkyleneglycol diallyl ether having a carbon number of 2 to 20, 1,4-cyclohexanedimethanol diallyl ether, tricyclo[5.2.1.$0^{2,6}$]decanedimethanol diallyl ether, and a compound represented by the following formula (4):

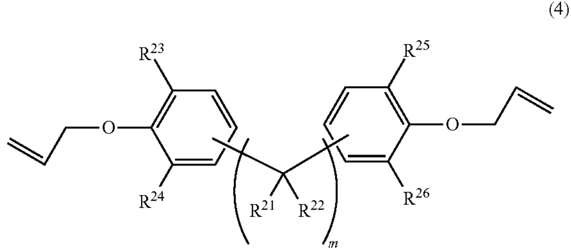

(4)

{wherein each of $R^{21}$ and $R^{22}$ is independently a hydrogen atom, an alkyl group having a carbon number of 1 to 6, a cycloalkyl group having a carbon number of 3 to 12 or an aryl group having a carbon number of 6 to 10, or $R^{21}$ and $R^{22}$ may combine together to form a cycloalkyl group having a carbon number of 3 to 12, each of $R^{23}$, $R^{24}$, $R^{25}$ and $R^{26}$ is independently a hydrogen atom, an alkyl group having a carbon number of 1 to 10, a cycloalkyl group having a carbon number of 3 to 12 or an aryl group having a carbon number of 6 to 10, and m represents an integer of 0 or 1}. Among these, a compound where each of $R^{21}$ to $R^{26}$ is independently a hydrogen atom or a methyl group and m is 1 or 0 is preferred.

Specific examples of such a compound include a diallyl ether of bisphenol-A, a diallyl ether of bisphenol-F, 2,6,2',6'-tetramethylbisphenol-A diallyl ether, 2,2'-diallylbisphenol-A diallyl ether, 2,2'-di-tert-butylbisphenol-A diallyl ether, 4,4'-biphenol diallyl ether, 2,2'-diisopropylbiphenol diallyl ether, 4,4'-ethylidenebisphenol diallyl ether, 4,4'-cyclohexylidenebisphenol diallyl ether, 4,4'-(1-α-methylbenzylidene) bisphenol diallyl ether, 4,4'-(3,3,5-trimethylcyclohexylidene)bisphenol diallyl ether, 4,4'-(1-methyl-benzylidene) bisphenol diallyl ether, and 3,3'-5,5'-tetramethyl-4,4'-biphenyldiol diallyl ether.

Examples of the compound where the number of allyl ether bonds is 3 or more include a phenol-formaldehyde and allyl alcohol polycondensate, and a cresol-formaldehyde and allyl alcohol polycondensate.

Incidentally, in the case of using an allyl ether bond-containing compound as the substrate to be epoxidized, the reactivity tends to be lower compared with the case of using a compound having a cyclohexene skeleton, and therefore, benzonitrile or trichloroacetonitrile is preferably used as the organic nitrile compound.

Usually, such a compound can undergo an epoxidation reaction only by mixing it with an aqueous hydrogen peroxide solution and a catalyst without using a solvent other than the organic nitrile compound itself. However, if desired, an alcohol-, hydrocarbon-, ester- or ether-based solvent may be also used.

In view of industrially stable production, the epoxidation method preferably comprises at first charging the substrate having a carbon-carbon double bond, the nitrile compound and the organic amine into a reaction vessel and gradually adding hydrogen peroxide while maintaining the reaction temperature as constant as possible. When such a method is employed, even if an oxygen gas is generated within the reaction vessel due to abnormal decomposition of hydrogen peroxide, the amount of hydrogen peroxide accumulated can be small and the increases in pressure can be minimized.

After the epoxidation reaction, the objective product may be extracted, if desired, by using an organic solvent, such as ethyl acetate, toluene, cyclohexane and hexane. The organic layer contains the raw material having a double bond and a by-product derived from the raw material, in addition to the objective product. Since hydrogen peroxide mostly migrates into the aqueous layer but is partially extracted in the organic layer, the organic layer may be treated with a reducing agent, such as sodium thiosulfate, to decompose hydrogen peroxide contained in the organic layer and then concentrated by distilling out the solvent, whereafter the objective product can be collected by a normal method, such as recrystallization, distillation and sublimation.

EXAMPLES

The present invention is described in greater detail below by referring to the Examples, but the present invention is not limited thereto.

Example 1

Into a 1,000 mL-volume three-neck flask equipped with a dropping funnel and a Dimroth condenser, 100 g (0.448 mol) of 3-cyclohexenylmethyl 3-cyclohexene-1-carboxylate, 183 g (4.48 mol) of acetonitrile and 4.53 g (0.0448 mol) of triethylamine were charged. The reaction solution was adjusted to 60° C., and 96.0 g (0.985 mol) of a 35% aqueous hydrogen peroxide solution was added dropwise with stirring over 2 hours while taking care to keep the reaction temperature from exceeding 65° C. After the completion of dropwise addition, stirring was continued for 8 hours, and the reaction solution was cooled to room temperature. The reaction solution was almost colorless transparent liquid, the conversion ratio of raw material was 68%, the yield of monoepoxide was 41%, and the yield of diepoxide was 27%.

Comparative Example 1

Into a 1,000 mL-volume three-neck flask equipped with a dropping funnel and a Dimroth condenser, 100 g (0.448 mol) of 3-cyclohexenylmethyl 3-cyclohexene-1-carboxylate, 300 ml of methanol, 73.5 g (1.79 mol) of acetonitrile and 7.7 g (0.077 mol) of potassium hydrogencarbonate were charged. To this suspension, 96.0 g (0.985 mol) of a 35% aqueous hydrogen peroxide solution was added dropwise over 2 hours at a reaction temperature in the range of 25 to 35° C., and after the completion of dropwise addition, stirring was continued for 8 hours. Subsequently, 100 ml of ethyl acetate was added to the reaction solution, and the product of the organic layer was analyzed. As a result, the conversion ratio of raw material was 87%, the yield of monoepoxide was 19%, and the yield of diepoxide was 43%. In addition, a by-product resulted from reacting the ester group of the raw material or reaction product with potassium hydrogencarbonate and saponificating, and moreover, a product resulted from reacting the by-product with the epoxy compound, and the reaction system became very complicated.

Examples 2 to 5

The reactions were carried out in the same manner as in Example 1 by changing the reaction conditions (liquid composition), and the results are shown in Table 1 together with the results of Example 1. Incidentally, in Example 5, a substrate different from that of Example 1 was used, but the concentration of the substrate was the same as in Example 1, i.e., 0.448 mol. In Example 4 using benzonitrile as the nitrile compound, the conversion ratio was higher compared with other Examples using acetonitrile and the reactivity was good. In Example 5, the conversion ratio was lower compared with Example 1 employing the same synthesis conditions, and the product was monoepoxide only. It was revealed that the reaction selectively occurs with the double bond of the cyclohexene skeleton.

Comparative Examples 2 and 3

Comparative Example 2 (the same as Example 1 except for not using triethylamine) and Comparative Example 3 (the same as Example 1 except for using ethanol (10 mol) in place of acetonitrile) were carried out. In both Comparative Examples 2 and 3, the reaction did not proceed. In Table 1, the mark "-" indicates that almost no reaction proceeded.

TABLE 1

| | | Kind, Concentration | | | | | | | | Time (hr) | | | Yield | |
|---|---|---|---|---|---|---|---|---|---|---|---|---|---|---|
| | | | Basic | | Molar Ratio | | | | Temp. | Dropwise | Reac- | Conv. | Mono- | Di- |
| | | Substrate | Compound | Nitrile | Substrate | Nitrile | Base | $H_2O_2$ | ° C. | Addition | tion | Ratio | epoxide | epoxide |
| Example | 1 | cyclohexenyl-methyl 3-cyclohexane-1-carboxylate | triethyl-amine | aceto-nitrile | 1 | 10 | 0.1 | 2.2 | 60 | 2 | 8 | 68% | 41% | 27% |
| | 2 | cyclohexenyl-methyl 3-cyclohexane-1-carboxylate | tributyl-amine | aceto-nitrile | 1 | 10 | 0.1 | 2.2 | 60 | 2 | 8 | 72% | 32% | 14% |
| | 3 | cyclohexenyl-methyl 3-cyclohexane-1-carboxylate | DBU | aceto-nitrile | 1 | 10 | 0.01 | 2.2 | 60 | 2 | 8 | 55% | 42% | 10% |
| | 4 | cyclohexenyl-methyl 3-cyclohexane-1-carboxylate | triethyl-amine | benzo-nitrile | 1 | 10 | 0.1 | 2.2 | 60 | 2 | 8 | 87% | 38% | 46% |
| | 5 | 3-cyclohexenyl-methyl methacrylate | triethyl-amine | aceto-nitrile | 1 | 10 | 0.1 | 2.2 | 60 | 2 | 8 | 55% | 48% | — |
| Comp. Example | 2 | cyclohexenyl-methyl 3-cyclohexane-1-carboxylate | none | aceto-nitrile | 1 | 10 | 0.1 | 2.2 | 60 | 2 | 8 | — | — | — |
| | 3 | cyclohexenyl-methyl 3-cyclohexane-1-carboxylate | triethyl-amine | ethanol | 1 | 0 | 0.1 | 2.2 | 60 | 2 | 8 | — | — | — |

DBU: 1,8-diazabicyclo[5.4.0]undecene-7

Comparative Examples 2 and 3: Almost no reaction proceeded.

Example 6

Into a 1,000 mL-volume three-neck flask equipped with a dropping funnel and a Dimroth condenser, 100 g (0.324 mol) of bisphenol-A diallyl ether, 334 g (3.24 mol) of benzonitrile and 16.4 g (0.162 mol) of triethylamine were charged. The reaction solution was adjusted to 80° C., and 69.33 g (0.985 mol) of a 35% aqueous hydrogen peroxide solution was added dropwise with stirring over 1 hour while taking care to keep the reaction temperature from exceeding 85° C. After the completion of dropwise addition, stirring was continued for 24 hours, and the reaction solution was cooled to room temperature. The reaction solution was almost colorless transparent liquid, the conversion ratio of raw material was 48%, the yield of monoepoxide was 33%, and the yield of diepoxide was 8%.

Examples 7 to 10

The reactions were carried out in the same manner as in Example 6 by changing the reaction conditions (liquid composition), and the results are shown in Table 2 together with the results of Example 6. Incidentally, in each Example, the concentration of the substrate was the same as in Example 6, i.e., 0.324 mol. The reactivity was slightly low compared with Examples 1 to 5, but it was revealed that the reaction occurs on all substrates.

TABLE 2

| | Kind, Concentration | | | | | | | | Time (hr) | | | Yield | |
|---|---|---|---|---|---|---|---|---|---|---|---|---|---|
| | | Basic | | Molar Ratio | | | | Temp. | Dropwise | Reac- | Conv. | Mono- | Di- |
| Example | Substrate | Compound | Nitrile | Substrate | Nitrile | Base | $H_2O_2$ | ° C. | Addition | tion | Ratio | epoxide | epoxide |
| 6 | bisphenol-A diallyl ether | triethyl-amine | benzo-nitrile | 1 | 10 | 0.5 | 2.2 | 80 | 1 | 24 | 48% | 33% | 8% |
| 7 | bisphenol-F diallyl ether | triethyl-amine | benzo-nitrile | 1 | 10 | 0.5 | 2.2 | 80 | 1 | 24 | 45% | 28% | 9% |
| 8 | 3,3',5,5'-tetramethyl-biphenyl-4,4'-diol diallyl ether | triethyl-amine | benzo-nitrile | 1 | 10 | 0.5 | 2.2 | 90 | 1 | 24 | 59% | 35% | 15% |
| 9 | 1,6-hexanediol diallyl ether | triethyl-amine | benzo-nitrile | 1 | 10 | 0.2 | 2.2 | 60 | 1 | 24 | 78% | 44% | 29% |
| 10 | 1,4-cyclo-hexanediol diallyl ether | triethyl-amine | benzo-nitrile | 1 | 10 | 0.2 | 2.2 | 60 | 1 | 24 | 75% | 49% | 24% |

INDUSTRIAL APPLICABILITY

According to the process for producing an epoxy compound of the present invention, a polyfunctional epoxy monomer that is widely used in various industrial fields including chemical industry as a raw material of resist materials (particularly, solder resist materials) or as a raw material of various polymers, such as agricultural/pharmaceutical intermediate, plasticizer, adhesive and coating resin, can be safely produced through a reaction of corresponding polyolefins with hydrogen peroxide by a simple operation with good yield at a low cost. Therefore, the process for producing an epoxy compound of the present invention is utilizable in various industries.

The invention claimed is:

1. A process for producing an epoxy compound, comprising epoxidizing a carbon-carbon double bond of an organic compound having a carbon-carbon double bond by using hydrogen peroxide as an oxidant, wherein the epoxidation is carried out by using an organic nitrile compound and an organic amine compound without using a metal compound.

2. The process for producing an epoxy compound as claimed in claim 1, wherein said organic nitrile compound is at least one member selected from acetonitrile, propionitrile, butyronitrile, isobutyronitrile, benzonitrile and trichloroacetonitrile.

3. The process for producing an epoxy compound as claimed in claim 1, wherein said organic amine compound is at least a tertiary amine.

4. The process for producing an epoxy compound as claimed in claim 1, wherein said organic-compound having a carbon-carbon double bond is an organic compound having a cyclohexene skeleton.

5. A process for producing an epoxy compound, comprising epoxidizing a carbon-carbon double bond of an organic compound having a carbon-carbon double bond by using hydrogen peroxide as an oxidant, wherein the epoxidation is carried out by using an organic nitrile compound and an organic amine compound, wherein said organic compound having a carbon-carbon double bond is at least one compound represented by the following formula (1):

(1)

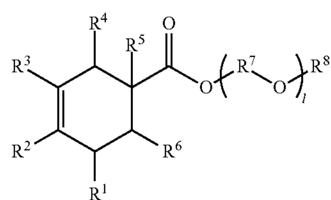

wherein each of $R^1$, $R^2$, $R^3$, $R^4$ and $R^5$ is independently a hydrogen atom or a methyl group, $R^6$ is a hydrogen atom, a methyl group, a phenyl group or $R^9$ represented by the following formula (2):

(2)

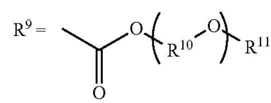

wherein $R^{10}$ is an alkylene group having a carbon number of 2 to 8 or a cycloalkylene group having a carbon number of 4 to 8, $R^{11}$ is an alkyl group having a carbon number of 1 to 10, a cycloalkyl group having a carbon number of 4 to 8, an aryl group having a carbon number of 6 to 10, an alkenyl group having a carbon number of 2 to 10 or a cycloalkenyl group having a carbon number of 4 to 8, and x is an integer of 0 to 5, $R^7$ is an alkylene group having a carbon number of 2 to 8 or a cycloalkylene group having a carbon number of 4 to 8, $R^8$ is an alkyl group having a carbon number of 1 to 10, a cycloalkyl group having a carbon number of 4 to 8, an aryl group having a carbon number of 6 to 10, an alkenyl group having a carbon number of 2 to 10 or a cycloalkenyl group having a carbon number of 4 to 8, and l is an integer of 0 to 5 and/or the following formula (3):

(3)

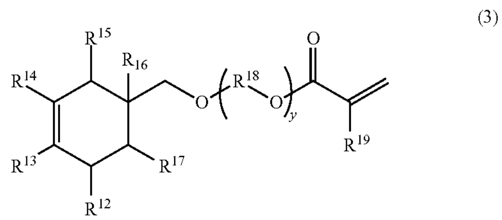

wherein each of $R^{12}$, $R^{13}$, $R^{14}$, $R^{15}$, $R^{16}$ and $R^{17}$ is independently a hydrogen atom or a methyl group, $R^{18}$ is an alkylene group having a carbon number of 2 to 8 or a cycloalkylene group having a carbon number of 4 to 8, $R^{19}$ is a hydrogen atom, a methyl group or a phenyl group, and y is an integer of 0 to 5.

6. A process for producing an epoxy compound, comprising epoxidizing a carbon-carbon double bond of an organic compound having a carbon-carbon double bond by using hydrogen peroxide as an oxidant, wherein the epoxidation is carried out by using an organic nitrile compound and an organic amine compound, wherein said organic compound having a carbon-carbon double bond is an organic compound having an allyl ether bond.

7. The process for producing an epoxy compound as claimed in claim 6, wherein said organic compound having a carbon-carbon double bond has a structure represented by the following formula (4):

(4)

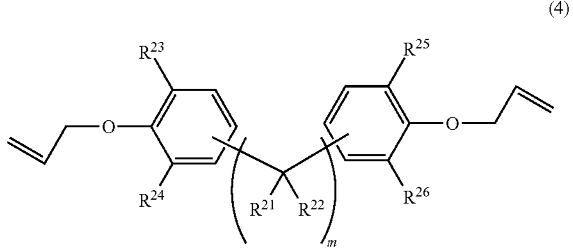

wherein each of $R^{21}$ and $R^{22}$ is independently a hydrogen atom, an alkyl group having a carbon number of 1 to 6, a cycloalkyl group having a carbon number of 3 to 12 or an aryl group having a carbon number of 6 to 10, or $R^{21}$ and $R^{22}$ may combine together to form a cycloalkyl group having a carbon number of 3 to 12, each of $R^{23}$, $R^{24}$, $R^{25}$ and $R^{26}$ is independently a hydrogen atom, an alkyl group having a carbon number of 1 to 10, a cycloalkyl group having a carbon number of 3 to 12 or an aryl group having a carbon number of 6 to 10, and m represents an integer of 0 or 1) 1.

8. The process for producing an epoxy compound as claimed in claim 6, wherein said compound having an allyl ether bond is at least one member selected from the group consisting of a diallyl ether of bisphenol-A, a diallyl ether of bisphenol-F, and 3,3'-5,5'-tetramethyl-4,4'-biphenyldiol diallyl ether.

9. The process for producing an epoxy compound as claimed in claim 6, wherein said compound having an allyl ether bond is at least one member selected from the group consisting of an α,ω-polyalkyleneglycol diallyl ether having a carbon number of 2 to 20, 1,4-cyclohexanedimethanol diallyl ether and tricyclo[5.2.1.$0^{2,6}$]decanedimethanol diallyl ether.

10. The process for producing an epoxy compound as claimed in claim 1, wherein said organic nitrile compound is used for the organic compound having a carbon-carbon double bond to be epoxidized so that a nitrile group in said organic nitrile compound is in a ratio of 0.8 to 40 molar equivalents based on the number of carbon-carbon double bonds of said organic compound.

11. The process for producing an epoxy compound as claimed in claim 1, wherein said hydrogen peroxide is an aqueous hydrogen peroxide solution at 20 to 65 mass %.

12. The process for producing an epoxy compound as claimed in claim 1, wherein said organic amine compound is used for the organic compound having a carbon-carbon double bond to be epoxidized so that an amine group in said organic amine compound is in a ratio of 0.001 to 2 molar equivalents based on the number of carbon-carbon double bonds of said organic compound.

13. The process for producing an epoxy compound as claimed in claim 2, wherein said organic nitrile compound is used for the organic compound having a carbon-carbon double bond to be epoxidized so that a nitrile group in said organic nitrile compound is in a ratio of 0.8 to 40 molar equivalents based on the number of carbon-carbon double bonds of said organic compound.

14. The process for producing an epoxy compound as claimed in claim 3, wherein said organic nitrile compound is used for the organic compound having a carbon-carbon double bond to be epoxidized so that a nitrile group in said organic nitrile compound is in a ratio of 0.8 to 40 molar equivalents based on the number of carbon-carbon double bonds of said organic compound.

15. The process for producing an epoxy compound as claimed in claim 4, wherein said organic nitrile compound is used for the organic compound having a carbon-carbon double bond to be epoxidized so that a nitrile group in said organic nitrile compound is in a ratio of 0.8 to 40 molar equivalents based on the number of carbon-carbon double bonds of said organic compound.

16. The process for producing an epoxy compound as claimed in claim 5, wherein said organic nitrile compound is used for the organic compound having a carbon-carbon double bond to be epoxidized so that a nitrile group in said organic nitrile compound is in a ratio of 0.8 to 40 molar equivalents based on the number of carbon-carbon double bonds of said organic compound.

17. The process for producing an epoxy compound as claimed in claim 6, wherein said organic nitrile compound is used for the organic compound having a carbon-carbon double bond to be epoxidized so that a nitrile group in said organic nitrile compound is in a ratio of 0.8 to 40 molar equivalents based on the number of carbon-carbon double bonds of said organic compound.

18. The process for producing an epoxy compound as claimed in claim 7, wherein said organic nitrile compound is used for the organic compound having a carbon-carbon double bond to be epoxidized so that a nitrile group in said organic nitrile compound is in a ratio of 0.8 to 40 molar equivalents based on the number of carbon-carbon double bonds of said organic compound.

19. The process for producing an epoxy compound as claimed in claim 8, wherein said organic nitrile compound is used for the organic compound having a carbon-carbon double bond to be epoxidized so that a nitrile group in said organic nitrile compound is in a ratio of 0.8 to 40 molar equivalents based on the number of carbon-carbon double bonds of said organic compound.

20. The process for producing an epoxy compound as claimed in claim 9, wherein said organic nitrile compound is used for the organic compound having a carbon-carbon double bond to be epoxidized so that a nitrile group in said organic nitrile compound is in a ratio of 0.8 to 40 molar equivalents based on the number of carbon-carbon double bonds of said organic compound.

21. The process for producing an epoxy compound as claimed in 2, wherein said hydrogen peroxide is an aqueous hydrogen peroxide solution at 20 to 65 mass %.

22. The process for producing an epoxy compound as claimed in 3, wherein said hydrogen peroxide is an aqueous hydrogen peroxide solution at 20 to 65 mass %.

23. The process for producing an epoxy compound as claimed in 4, wherein said hydrogen peroxide is an aqueous hydrogen peroxide solution at 20 to 65 mass %.

24. The process for producing an epoxy compound as claimed in 5, wherein said hydrogen peroxide is an aqueous hydrogen peroxide solution at 20 to 65 mass %.

25. The process for producing an epoxy compound as claimed in 6, wherein said hydrogen peroxide is an aqueous hydrogen peroxide solution at 20 to 65 mass %.

26. The process for producing an epoxy compound as claimed in 7, wherein said hydrogen peroxide is an aqueous hydrogen peroxide solution at 20 to 65 mass %.

27. The process for producing an epoxy compound as claimed in 8, wherein said hydrogen peroxide is an aqueous hydrogen peroxide solution at 20 to 65 mass %.

28. The process for producing an epoxy compound as claimed in 9, wherein said hydrogen peroxide is an aqueous hydrogen peroxide solution at 20 to 65 mass %.

29. The process for producing an epoxy compound as claimed in claim 2, wherein said organic amine compound is used for the organic compound having a carbon-carbon double bond to be epoxidized so that an amine group in said organic amine compound is in a ratio of 0.001 to 2 molar equivalents based on the number of carbon-carbon double bonds of said organic compound.

30. The process for producing an epoxy compound as claimed in claim 3, wherein said organic amine compound is used for the organic compound having a carbon-carbon double bond to be epoxidized so that an amine group in said organic amine compound is in a ratio of 0.001 to 2 molar equivalents based on the number of carbon-carbon double bonds of said organic compound.

31. The process for producing an epoxy compound as claimed in claim 4, wherein said organic amine compound is used for the organic compound having a carbon-carbon double bond to be epoxidized so that an amine group in said organic amine compound is in a ratio of 0.001 to 2 molar equivalents based on the number of carbon-carbon double bonds of said organic compound.

32. The process for producing an epoxy compound as claimed in claim 5, wherein said organic amine compound is used for the organic compound having a carbon-carbon double bond to be epoxidized so that an amine group in said organic amine compound is in a ratio of 0.001 to 2 molar equivalents based on the number of carbon-carbon double bonds of said organic compound.

33. The process for producing an epoxy compound as claimed in claim 6, wherein said organic amine compound is used for the organic compound having a carbon-carbon double bond to be epoxidized so that an amine group in said organic amine compound is in a ratio of 0.001 to 2 molar equivalents based on the number of carbon-carbon double bonds of said organic compound.

34. The process for producing an epoxy compound as claimed in claim 7, wherein said organic amine compound is used for the organic compound having a carbon-carbon double bond to be epoxidized so that an amine group in said organic amine compound is in a ratio of 0.001 to 2 molar equivalents based on the number of carbon-carbon double bonds of said organic compound.

35. The process for producing an epoxy compound as claimed in claim 8, wherein said organic amine compound is used for the organic compound having a carbon-carbon double bond to be epoxidized so that an amine group in said organic amine compound is in a ratio of 0.001 to 2 molar equivalents based on the number of carbon-carbon double bonds of said organic compound.

36. The process for producing an epoxy compound as claimed in claim 9, wherein said organic amine compound is used for the organic compound having a carbon-carbon double bond to be epoxidized so that an amine group in said organic amine compound is in a ratio of 0.001 to 2 molar equivalents based on the number of carbon-carbon double bonds of said organic compound.

37. The process for producing an epoxy compound as claimed in claim 3, wherein said organic amine compound is a tertiary amine.

38. The process for producing an epoxy compound as claimed in claim 37, wherein said tertiary amine is selected from the group consisting of trimethylamine, N,N-dimethylethylamine, N,N-diethylmethylamine, N-butyldimethylamine, N,N-dimethylisopropylamine, triethylamine, tri-n-propylamine, tri-n-butylamine, triisobutylamine, tri-n-pentylamine, triisoamylamine, tri-n-octylamine, and tri-(2-ethylhexyl)amine.

* * * * *